US 6,712,805 B2
Weimann
Mar. 30, 2004

(54) METHOD AND APPARATUS FOR INTRADERMAL INCORPORATION OF MICROPARTICLES CONTAINING ENCAPSULATED DRUGS USING LOW FREQUENCY ULTRASOUND

(76) Inventor: Ludwig J. Weimann, 488 Ethan Allen Pkwy., Burlington, VT (US) 05401

( * ) Notice: Subject to any disclaimer, the term of this patent is extended or adjusted under 35 U.S.C. 154(b) by 0 days.

(21) Appl. No.: 10/058,627

(22) Filed: Jan. 28, 2002

(65) Prior Publication Data

US 2002/0138037 A1 Sep. 26, 2002

Related U.S. Application Data

(60) Provisional application No. 60/264,803, filed on Jan. 29, 2001.

(51) Int. Cl.$^7$ ............................................. A61M 31/00
(52) U.S. Cl. ........................................ 604/500; 604/22
(58) Field of Search ............................ 604/20, 22, 500, 604/501, 890.1; 601/2; 606/169–171, 128

(56) References Cited

U.S. PATENT DOCUMENTS

| | | | | |
|---|---|---|---|---|
| 4,691,724 A | * | 9/1987 | Garcia et al. ............ 134/169 R |
| 4,767,402 A | | 8/1988 | Kost ........................... 604/22 |
| 4,844,882 A | * | 7/1989 | Widder et al. .............. 424/9.52 |
| 5,016,615 A | * | 5/1991 | Driller et al. .................. 601/2 |
| 5,384,133 A | | 1/1995 | Boyes ......................... 424/501 |
| 5,421,816 A | | 6/1995 | Lipkovker .................... 604/20 |
| 5,688,233 A | | 11/1997 | Hofmann ..................... 604/20 |
| 5,814,599 A | | 9/1998 | Mitragotri ...................... 514/3 |
| 5,947,921 A | | 9/1999 | Johnson ........................ 604/22 |
| 6,024,717 A | * | 2/2000 | Ball et al. ..................... 604/22 |
| 6,030,374 A | * | 2/2000 | McDaniel .................... 604/506 |
| 6,143,276 A | * | 11/2000 | Unger ........................ 424/9.3 |
| 6,234,990 B1 | * | 5/2001 | Rowe et al. ................... 604/22 |
| 6,322,532 B1 | * | 11/2001 | D'Sa et al. ................... 604/22 |
| 6,385,487 B1 | * | 5/2002 | Henley ......................... 604/20 |
| 6,416,740 B1 | * | 7/2002 | Unger ........................ 424/9.52 |
| 6,464,680 B1 | * | 10/2002 | Brisken et al. .............. 604/501 |
| RE38,000 E | * | 2/2003 | Henley ......................... 604/20 |

* cited by examiner

Primary Examiner—Brian L. Casler
Assistant Examiner—Cris Rodriguez
(74) Attorney, Agent, or Firm—Elman Technology Law, P.C.; Gerry J. Elman

(57) ABSTRACT

An apparatus for sonoporation for transdermal delivery of a microparticles suspension containing microencapsulated drugs includes a container having an end covered with a porous membrane and containing said microparticles suspension and an ultrasound horn having a tip submerged in said microparticles suspension containing microencapsulated drugs. The ultrasound horn applies ultrasound radiation to the microparticles suspension containing microencapsulated drugs. The ultrasound radiation is applied at a frequency, an intensity, for a period of time, and at a distance from the skin, effective to generate cavitation bubbles, wherein the cavitation bubbles collapse and transfer their energy into the skin area thus causing the formation of pores in the skin area; and wherein the ultrasound radiation intensity and distance from the skin area are also effective in generating ultrasonic jets, the ultrasonic jets driving the microparticles suspension containing microencapsulated drugs through a porous membrane and the formed pores into the skin area. The ultrasound radiation can optionally have a frequency of 1 KHz to 5 MHz.

43 Claims, 6 Drawing Sheets

METHOD AND APPARATUS FOR INTRADERMAL INCORPORATION OF MICROPARTICLES CONTAINING ENCAPSULATED DRUGS USING LOW FREQUENCY ULTRASOUND

This application claims the benefit of U.S. Provisional Application No. 60/264,803 filed on Jan. 29, 2001.

FIELD OF THE INVENTION

This invention relates to a method and apparatus for in vivo intradermal incorporation of micro-particles containing encapsulated drugs or a therapeutic agent or cosmetic for topical or subcutaneous application using low frequency ultrasound.

BACKGROUND OF THE INVENTION

Intradermal delivery of drugs offers several advantages over conventional delivery methods including oral and injection methods. It delivers a predetermined drug dose to a localized area with a controlled steady rate and uniform distribution, is non-invasive, convenient and painless.

U.S. application Ser. No. 09/690,604, commonly assigned and incorporated by reference, describes a method and apparatus for sonoporation of biological barriers such as Stratum Corneum (SC), most commonly referred to as the outermost layer of human skin. Sonoporation is the noninvasive transdermal delivery of pharmaceutical drug molecules through the SC and into the cardiovascular system a human body via ultrasound radiation.

Significant improvement made to existing sonoporation and sonophoresis methods of transdermal drug delivery may be leveraged to increase market share. Drug encapsulation is a known practice in therapeutic application of the potent but very unstable drugs. Using sonoporation and sonophoresis in the area of delivery of encapsulated drugs would provide many additional pharmaceutical benefits compared to the benefits of a present ways of sonoporetic or sonophoresic drug delivery. Some of these benefits would include delivery of peptide-based drugs that range from bed-wetting to gastric bleeding to cancer and immune disorders such as HIV.

SUMMARY OF THE INVENTION

In one aspect, the invention provides for an apparatus for sonoporation for intradermal delivery of a microparticles suspension containing microencapsulated drugs including a container having an end covered with a porous membrane and containing the microparticles suspension; an ultrasound horn having a tip submerged in the microparticles suspension containing microencapsulated drugs and applying ultrasound radiation to the microparticles suspension containing microencapsulated drugs wherein the ultrasound radiation is applied at a frequency, an intensity, for a period of time, and at a distance from the skin, effective to generate cavitation bubbles, wherein the cavitation bubbles collapse and transfer their energy into the skin area thus causing the formation of pores in the skin area; and wherein the ultrasound radiation intensity and distance from the skin area are also effective in generating ultrasonic jets, the ultrasonic jets driving the microparticles suspension containing microencapsulated drugs through a porous membrane and the formed pores into the skin area.

Implementations of the invention may include one or more of the following features. The membranes may have pores with a diameter of 100 micrometers. The ultrasound radiation has a frequency in the range of 1 KHz and 1 MHz. The membrane may be hydrophobic. The tip may be removably connected to the ultrasound horn and it may have a distal end surface, which may be flat or concave. The distal end surface may have a plurality of depressions. The tip may also have a body having markings indicating the amount of microparticles suspension containing microencapsulated drugs contained in the container. A removable protective film may cover the membrane. The container may include an outer wall, an inner wall and an absorbent wick placed between the inner and outer wall. The wick absorbs any excess microparticles suspension containing microencapsulated drugs that is not driven into the skin area through the formed pores and it may be made of highly absorbent and hydrophilic material such as PVA sponge CLINICEL™ from M-Pact Company, HYDROFERA PVA sponge from Hydrofera LLC, Sodium CMC and any other similar spongy material. The container inner wall may have first and second grooves and the tip may have a body having first and second grooves. The tip is inserted into the container and placed so that the first and second grooves of the tip body are opposite the first and second grooves of the container inner wall. This arrangement defines the first and second spaces for accommodating the first and second o-rings, respectively. The container may also have an inlet septum for filling it with the solution. The container may be a cylinder made of a transparent material and/or a plastic material.

The ultrasound frequency may be 20 KHz and the ultrasound intensity may be in the range of 5 W/cm$^2$ and 55 W/cm$^2$. The tip may have a distal end located at a distance from the membrane in the range of 1 millimeter to 10 millimeters. The ultrasound radiation may be continuous or pulsed and it may be applied for a period of time in the range of 30 seconds to 5 minutes, preferably 1 minute for continuous exposure or about 10 to 20 minutes for pulsed exposure with a 5% duty cycle, respectively. The formed pores may have a diameter in the range of 1 micrometer to 100 micrometers.

In another aspect, the invention features a method for sonoporation for intradermal delivery of a microparticles suspension containing microencapsulated drugs. The method includes providing a container containing a predetermined amount of said microparticles suspension containing microencapsulated drugs, or therapeutic agents, or cosmetics and having a first end and a second end, said second end being covered with a porous membrane. Next the tip of an ultrasound horn is submerged in the microparticles suspension containing microencapsulated drugs through the first end of the container and then the porous membrane is placed in contact with said skin area. The ultrasound radiation is applied at a frequency, and intensity, for a period of time, and at a distance from the skin, effective to generate cavitation bubbles. The cavitation bubbles collapse and transfer their energy into the skin area thus causing the formation of pores in the skin area. The ultrasound radiation intensity and distance from the skin area are also effective in generating ultrasonic jets, the ultrasonic jets driving the microparticles suspension containing microencapsulated drugs, therapeutic agents and cosmetics through a porous membrane and the formed pores into the skin area.

In a further aspect, the ultrasound radiation can then applied at a frequency in the range of 1 KHz and 1 MHz.

One advantage of the present invention is to protect against any unknown effects of ultrasound and cavitation on drugs, or therapeutic agents or cosmetics.

A second advantage of the present invention is the controlled release of drugs, or therapeutic agents over time into the stratum corneum and subsequently into the human vascular system. This invention can be used to provide slow and constant intradermal release of drugs, or therapeutic agents or cosmetics.

A third advantage of the present invention is to reduce the need for repeated dosage of drugs, or therapeutic agents since time-released drugs, or therapeutic agents can be administered once and not require repeating for longer periods of time than dosages required using conventional methods.

A fourth advantage of the present invention is the ability to apply sensitive, non-soluble or unstable drugs, or therapeutic agents. Drugs, or therapeutic agents or cosmetics can be specially engineered to retain full potency in a stable environment within the micro-particle until it is delivered using sonoporation. The encapsulation prevents the premature breakdown of drugs or active agents or cosmetic before they can be effectively delivered into or through the skin.

A fifth advantage of the present invention is that the delivery of the drugs and therapeutic agents is painless compared to the side effects or the discomfort and pain associated with injection.

BRIEF DESCRIPTION OF THE DRAWINGS

FIG. 1 is a cross sectional side view of an apparatus for intradermal delivery of micro-particles using ultrasound.

FIG. 1A is a cross sectional side view of an alternative embodiment of the tip, i.e. the UTDDA, shown in FIG. 1.

FIG. 2 is a cross sectional side view of an ultrasonic transdermal drug delivery applicator (UTDDA) using micro-particles containing encapsulated drugs and therapeutic agents and cosmetics.

FIG. 3 is a graphic transcription of the confocal microscopy image of the cross-section of the upper part of the skin after 15 seconds exposure to 20 kHz ultrasound at intensity of 19 W/cm$^2$ in aqueous suspension of 1 $\mu$m particles.

FIG. 4 is a cross sectional of a micro-particle containing encapsulated drugs, or therapeutic agents or cosmetics.

FIG. 5 is a cross sectional side view of a Franz Cell apparatus for determining infusion of micro-particles into the human cadaver epidermis.

FIG. 6 is a flow chart of a method for transdermal incorporation of micro-particles containing encapsulated substance using 20 kHz ultrasound.

DETAILED DESCRIPTION OF THE DRAWINGS

The present invention is an apparatus and method for intradermal incorporation of micro-particles containing encapsulated drugs, or therapeutic agents or cosmetics using sonoporation. The apparatus is designed to use ultrasound to deliver a suspension of micro-particles into the epidermal layer of the skin. The micro-particles contain medication or cosmetic that is encapsulated to provide protection. The encapsulation also provides means of controlled released of the drug, or therapeutic agents or cosmetic into the skin.

FIG. 1 shows a sonoporation device 6 used for in vitro sonoporation of skin that includes an ultrasound equipment assembly 20, electrically and mechanically connected to an ultrasonic transdermal drug delivery applicator (UTDDA) 100 (described in detail below) via an ultrasonic horn 80. The ultrasound equipment assembly 20 includes an ultrasound transducer 50, which in turn is electrically connected to power supply 30 via connecting cable 40.

In operation, the UTDDA 100 is removably connected to the affected skin surface via pressure resistive adhesive. Ultrasonic horn 80 is placed inside the UTDDA 100. Power supply 30 is activated and provides power to ultrasonic transducer 50. The ultrasonic transducer 50 converts electrical energy into acoustic pressure waves that are coupled through the ultrasonic horn 80 and into the UTDDA 100. Sonoporation of the affected skin occurs for a predetermined interval, which depending upon skin resistivity and can range from 5 to 60 seconds.

As shown in FIG. 1, the distal end surface of the UTDDA is flat. As shown in FIG. 1A, the distal end surface of an alternative embodiment of the UTDDA is concave.

FIG. 2 is a schematic of the ultrasonic transdermal drug delivery applicator (UTDDA) 100 that includes an inner applicator wall 201, an outer applicator wall 202, a first O-ring 220, a second O-ring 230, a wick 250, a microparticles suspension inlet septum 240, a solution level marking 260, a removable protective film 265, a porous membrane 280, a microparticles suspension 290 that includes microparticles containing encapsulated drugs. The figure also shows parts of the ultrasonic horn 80, including a tip of ultrasonic horn 210, and a bottom of ultrasonic horn tip 270.

The UTDDA 100 is a hollow cylindrically shaped object, preferably made of a transparent hard plastic material and is discarded after use. Between the outer applicator wall 202 and the inner applicator wall 201 is a wick 250, made of material such as high-absorbency polypropylene. Both the inner and outer applicator walls 201 and 202 are basically cylindrical and axially aligned, with the exception of two locations on the inner applicator wall 201 where two grooves are cut on the inside surface of the inner applicator wall 201 for the two O-rings 220 and 230 to fit into the assembly. The location and orientation of the grooves, and the two O-rings 220 and 230 are shown in FIG. 2. As shown in FIG. 2, grooves cut into the outer diameter of the ultrasonic horn 80 are matched to the placement of the O-rings 220 and 230 to facilitate a secure fit between the UTDDA 100 and the ultrasonic horn 80.

Again in reference to FIG. 2, the drug inlet septum 240 is located between the outer applicator wall 202 and the inner applicator wall 201 approximately halfway between the top and bottom of the UTDDA 100. The septum is constructed of a silicon rubber material, designed to be impervious to liquids yet allow injection of the microparticles suspension into the UTDDA 100 using a hypodermic needle. The solution marking level 260 is pre-marked on the side of the UTDDA 100 to indicate the proper volumetric measure of microparticles suspension to be administered.

At the base of the UTDDA 100, the porous membrane 280 is fixedly attached to the inner applicator wall 201. The membrane 280, constructed of a non-woven polypropylene or other similar hydrophobic material, resists the passage of the aqueous liquid due to its non-wettable surface and small diameter of the pores in range of 1–100 microns. A removable protective film 265, which is preferably a thin plastic sheet, is removeably connected to the porous membrane 280 using silicon or other medical adhesive.

In operation, the sterilized UTDDA 100 is placed over the tip of ultrasonic horn 210 with the two O-rings 220 and 230 in place as shown in FIG. 2. The micro-particle suspension 290 with suspended micro-particles containing encapsulated drugs is introduced into the reservoir of the UTDDA 100 through the inlet septum 240 using a hypodermic needle (not shown) to inject a pre-measured amount of micro-particle suspension 290. The protective film 265 is peeled off to expose the porous membrane 280. When the UTDDA 100 is properly filled, the tip of the ultrasonic horn 210 is partially immersed in the micro-particle suspension 290. Visual inspection of the solution level marking 260 indicates whether the applicator is properly filled, and whether the UTDDA 100 is leaking or defective.

Once the UTDDA 100 is filled and determined to be ready for use, the apparatus is placed on the skin, oriented such that the porous membrane 280 is flush with the location where the drugs are to be administered and such that the bottom of the horn tip 270 is immersed in micro-particle suspension 290. A timer (not shown), which is contained in power supply 30, is set to a predetermined length of time for sonoporation. The power supply is switched on, and the ultrasound sonoporates the skin for an allotted amount of time. The porous membrane 280 is designed to prevent the microparticles suspension from leaking prior to transdermal infusion process, yet simultaneously allow ultrasound waves to freely pass through the membrane 280 and sonoporate the skin surface. Any excess liquid that is transferred to the skin during the ultrasound exposure is absorbed by the wick 250. After use, the UTDDA 100 is removed form the ultrasound tip and discarded.

Figure 1:
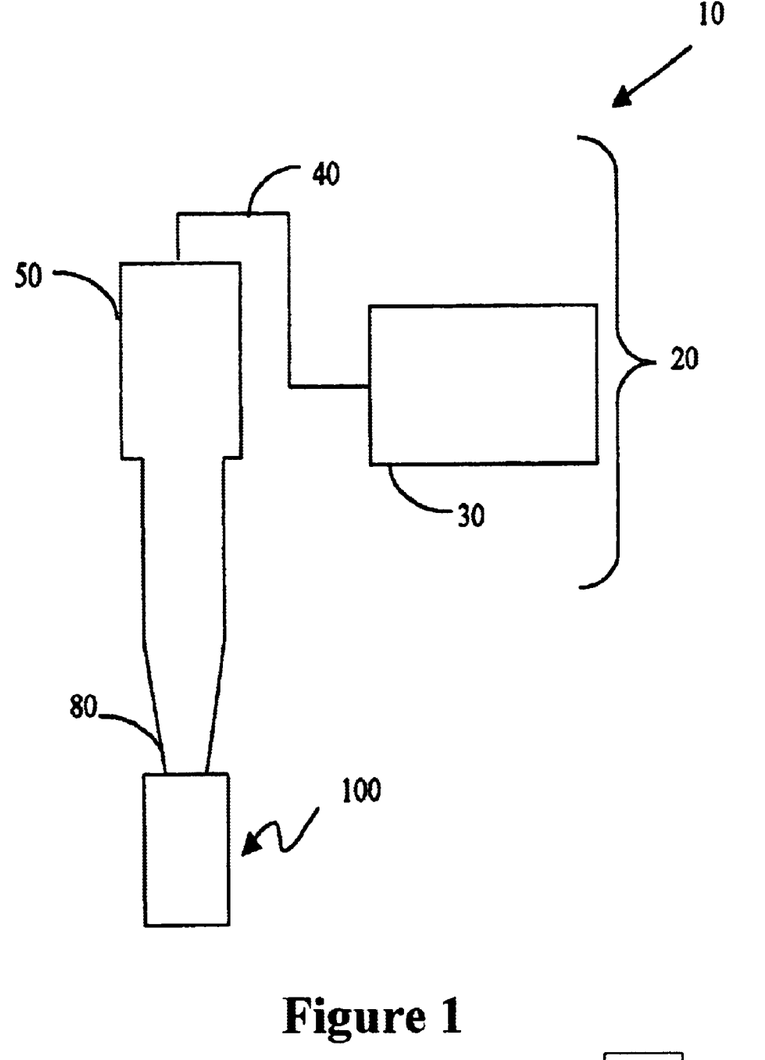
Figure 1A:
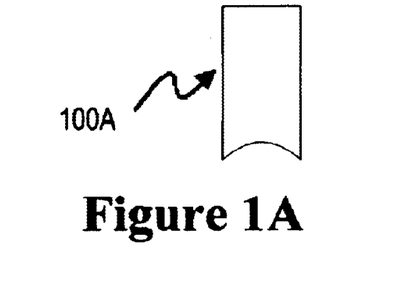
Figure 2:
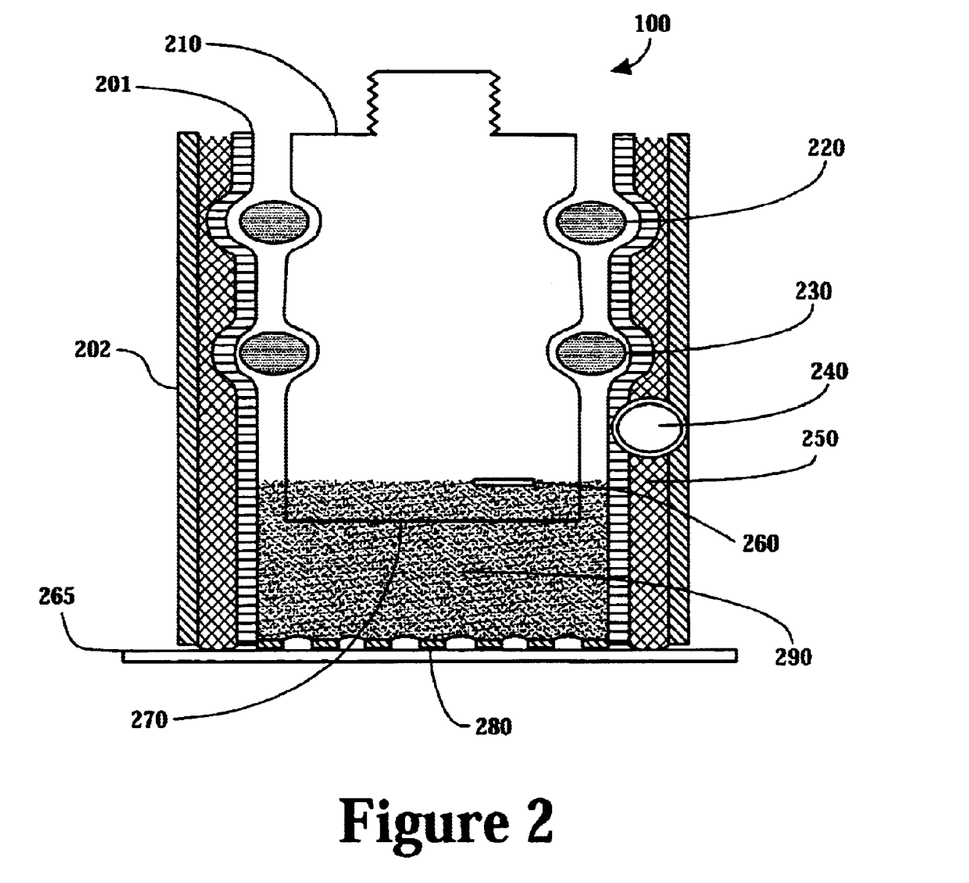
Figure 3:
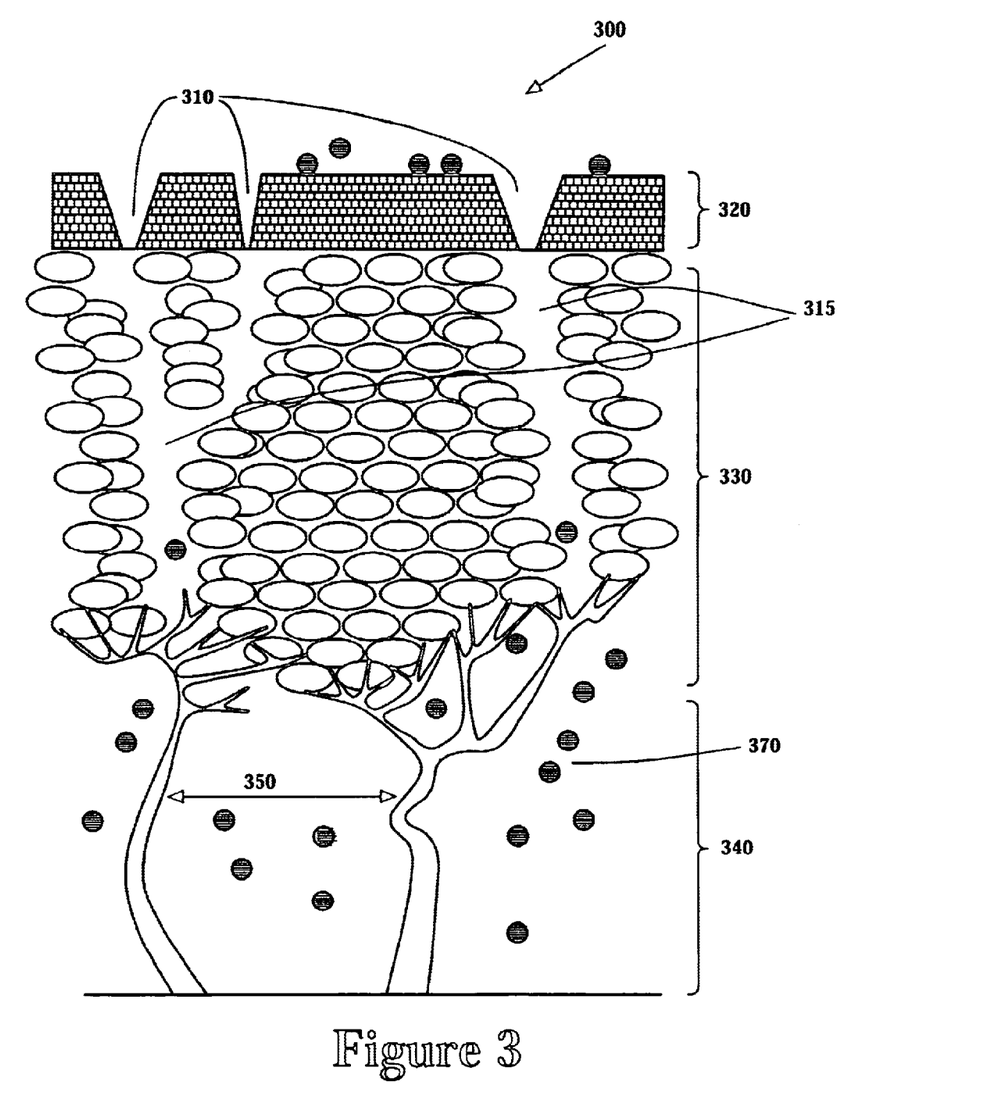

FIG. 3 shows a skin system 300 that represents a cross section of human skin after exposure to 20 kHz ultrasound in presence of the suspension of the 1 $\mu$m particles in aqueous saline solution. The figure shows the environment where the drug, therapeutic agent, or cosmetic, which is encapsulated in the micro-particle is delivered into the skin by action of the 20 kHz ultrasound. The cross-section of the skin includes a stratum corneum (the top part of the skin) 320, an underlying layer called the viable epidermis 330, and a dermis 340. Between the epidermal and dermal layers reside the endings of a capillary vascular system 350. Pores 310 in the stratum corneum 320 and the transient micropores 315 in the viable epidermis 330 are created when the skin is exposed to ultrasound. The size of the pores in stratum corneum is in the range of 1 to 100 micrometers in diameter. The size of the micropores generated in viable epidermis is in range up to 35 micrometers in diameter. The ultrasound intensity is in the range of 11 W cm$^{-1}$ to 79 W cm$^{-1}$. The figure shows the micro-particles 370 migrating through the pores 310 in the stratum corneum 320 then through the transient micropores 315 in the viable epidermis 330 to part of the dermis with the capillary vascular system 350.

In operation, the microparticles suspension 290 containing the micro-particles 370 is delivered to the skin using the sonoporation apparatus. The ultrasound assists in propelling the micro-particles 370 through the pores 310 and transient micropores 315. Once the micro-particles are lodged in the epidermis, the drug, or therapeutic agent, or cosmetic is released from the micro-particles at a controlled rate determined by the micro-particle chemical composition. Subsequently the drug, or therapeutic agent released from the micro-particles is ultimately absorbed into the capillary vascular system 350.

Figure 4:
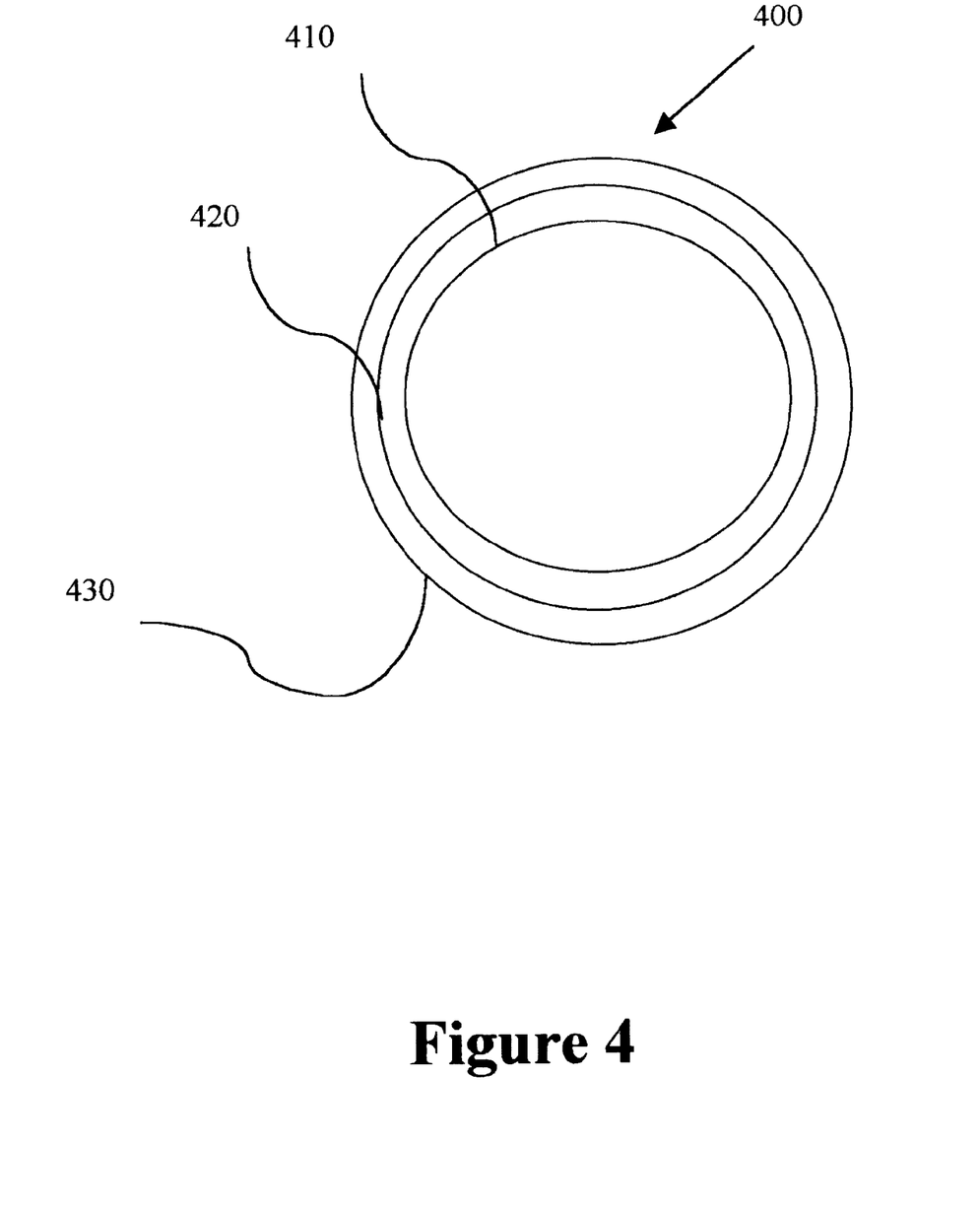

FIG. 4 shows a schematic of a cross-section of a micro-particle 400 containing a drug, or therapeutic agent, or cosmetic 410, a first protective sheath 420, and a second protective sheath 430. Microencapsulation is a known process in the pharmaceutical field and is not described here. Examples of other patents that address the method of creating and using micro-particles include U.S. Pat. Nos. 4,983,401, 5,792,477, 5,723,269, 6,048,550, and 5,651,990. The micro-particle 400 is generally spherical and includes one or more protective sheaths, arranged in concentric and incrementally smaller hollow spheres, with a center core sphere of encapsulated drug, or therapeutic agent, or cosmetic in a solid, liquid or solvated states. The content of encapsulated drugs, or therapeutic agent, or cosmetic 410 is shown in FIG. 4 at the center of the micro-particle 400.

In one example embodiment, drug or a therapeutic agent 410 includes anti-fungal agents, hormones, vitamins, peptides, enzymes, anti-allergic agents, anti-coagulation agents, antituberculars, antivirals, antibiotics, antibacterials, antiinflammatory agents, antiprotozoans, local anesthetics, growth factors, cardiovascular agents, diuretics, and radio-active compounds; scopolamine, nicotine, methylnicotinate, mechlorisone dibutyrate, naloxone, methanol, caffeine, salicylic acid, and 4-cyanophenol; anti-fungal agents selected from the group consisting of ketoconazole, nystatin, griseofulvin, flucytosine, miconazole, and amphotericin B; hormones selected from the group consisting of growth hormone, melanocyte stimulating hormone, estradiol, progesterone, testosterone, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methyl-prednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins selected from the group consisting of cyanocobalamin neinoic acid, retinoids, retinol palmitate, ascorbic acid, and alpha-tocopherol, B-12 and other vitamins; peptides and enzymes selected from the group consisting of manganese super oxide dismutase and alkaline phosphatase; the anti-allergic agent is amelexanox; the anti-coagulation agents selected from the group consisting of phenprocoumon and heparin; the antituberculars selected from the group consisting of paraminosalicylic acid, isoniazid, capreomycin sulfate cycloserine, ethambutol hydrochloride ethionamnide, pyrazinamide, rifampin, and streptomycin sulfate; the antivirals selected from the group consisting of acyclovir, amantadine azidothymidine, ribavirin and vidarabine monohydrate; the antibiotics selected from the group consisting of dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; the antiinflammatories selected from the group consisting of diflunisal, ibuprofen, indomethacin, meclofenamate, mefenamic acid, naproxen, oxyphenbutazone, phenylbutazone, piroxicam, diclofenac, sulindac, tolmetin, aspirin and salicylates; the antiprotozoans selected from the group consisting of chloroquine, hydroxychloroquine, metronidazole, quinine and meglumine antimonate; the local anesthetics selected from the group consisting of bupivacaine hydrochloride, chlorop-rocaine hydrochloride, etidocaine hydrochloride, lidocaine hydrochloride, mepivacaine hydrochloride, procaine hydrochloride and tetracaine hydrochloride; the growth factors selected from the group consisting of Epidermal Growth Factor, acidic Fibroblast Growth Factor, Basic Fibroblast Growth Factor, Insulin-Like Growth Factors, Nerve Growth Factor, Platelet-Derived Growth Factor, Stem Cell Factor, Transforming Growth Factor of the alpha family and Transforming Growth Factor of the beta family; the cardiovascular agents are selected from the group consisting of clonidine, propranolol, lidocaine, nicardipine and nitroglycerin; the diuretics are selected from the group consisting of mannitol and urea; and wherein the radioactive particles are selected from the group consisting of strontium, iodine, rhenium and yttrium.

In another example embodiment, therapeutic agent 410 includes the following:

(1) peptides selected from the group consisting of melanin concentrating hormone, melanin stimulating hormone, trypsin inhibitor, Bowman Burk inhibitor, luteinizing hormone releasing hormone, bombesin, cholecystokinin, insulin, gastrin, endorphins, enkephalins, growth hormone, prolactin, oxytocin, follicle stimulating hormone, human chorionic gonadotropin, corticotropin, .beta.-lipotropin, .gamma.-lipotropin, calcitonin, glucagon, thyrotropin, elastin, cyclosporin, and collagen;

(2) monoclonal antibodies;

(3) factors selected from the group consisting of hyaluronic acid, heparin, mad heparin sulfate;

(4) anti-sense peptides and anti-sense oligonucleotides selected from the group consisting of an antisense oligonucleotide capable of binding the DNA encoding at least a portion of Ras, an antisense oligonucleotide capable of binding the DNA encoding at least a portion of basic fibroblast growth factor, and the antisense ras/p53 peptide;

(5) immunosuppressants and anti-inflammatory agents;

(6) chelants and chelating agents selected from the group consisting of penicillamine, citrate, ascorbate, diethylenetriaminepentaacetic acid, dihydroxypropylethylenediamine, cyclohexanediaminetetraacetic acid, ethylenediaminetetraacetic acid, ethylene glycol-bis(.beta.-aminoethyl ether)N,N,N',N',-tetraacetic acid, etidronic acid, dimethylsulfoxide, dipyridoxylethylenediaminediacetate-bisphosphate, N,N'-(1,2-ethanediylbis(oxy-2,1-phenylene))bis(N-(carboxymethyl), aminophenoltriacetic acid, tetrakis(2-pyridylmethyl)ethylenediamine, cyanins, and salts thereof; and (7) DNA encoding at least a portion of the following genes: HLA, dystrophin, CFTR, interleukin-2, tumor necrosis factor, adenosine deaminase, HDL receptor, thymidine kinase, HLA-B7, interleukin-4, melanocyte stimulating hormone gene, and melanin concentrating hormone gene.

In yet another example embodiment, the cosmetic 410 includes Vitamin A, Vitamin C, Vitamin D, Vitamin E, Vitamin K, beta carotene, collagen, elastin, retinoic acid, aloe vera, lanolin, hyaluronic acid, and nucleosides; a sunscreen agent, said sunscreen agent selected from the group consisting of 5% isobutyl-p-aminobenzoate, 5% diallyl trioleate, 2.5% monoglyceryl p-aminobenzoate, 4% propylene glycol p-aminobenzoate, and a composition comprising 2% benzyl salicylate and 2% benzyl cinnamate; a cosmetic cream, ointment, lotion, skin softener, gel, blush, eye-liner, mascara, acne-medication, cold cream, cleansing cream, or oleaginous foam.

In another example embodiment, the composition 410 comprises one or more compounds selected from the following:

(1) bacteriostatic agents selected from the group consisting of benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid;

(2) antioxidants selected from the group consisting of tocopherol, ascorbic acid and ascorbyl palmitate;

(3) preservatives selected from the group consisting of parabens, quaternary ammonium compounds, alcohols, phenols, and essential oils;

(4) buffers and neutralizers;

(5) moisture content control agents and humectants;

(6) ointment bases selected from the group consisting of lanolin, lanolin anhydrous, hydrophilic ointment, white ointment, yellow ointment, polyethylene glycol ointment, petrolatum, hydrophilic petrolatum, white petrolatum, rose water ointment, and squalene;

(7) suspending and viscosity-increasing agents selected from the group consisting of acacia, agar, alginic acid, aluminum monostearate, bentonite, purified bentonite, magma bentonite, carbomer 934P, carboxymethylcellulose calcium, carboxymethylcellulose sodium 12, carboxymethylcellulose sodium, carrageenan, microcrystalline cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, silicon dioxide, zinc oxide, sodium alginate tragacanth, and xanthan gum;

(8) skin absorption enhancing agents selected from the group consisting of pyrrolidones, fatty acids, sulfoxides, amines, terpenes, terpenoids, surfactants, alcohols, urea, glycols, azone, n-alkanols, n-alkanes, orgelase, and alphaderm cream;

(9) bases selected from the group consisting of glycerol, propylene glycol, isopropyl myristate, urea in propylene glycol, ethanol and water, and polyethylene glycol;

(10) other agents selected from the group consisting of glycerin, hexylene glycol, sorbitol, propylene glycol, and calcium silicate;

(11) oleaginous vehicles;

(12) coloring agents; and (13) foaming agents.

In another example embodiment, the composition 410 comprises a gas in range of 0–50% in the interior of the micro-particle and an effective amount of drug, or therapeutic agent, or cosmetic.

A structural composition of the micro-particle 370 or 400 can vary depending on the content of the micro-particle and the method of the release of that content once the micro-particles are embedded in the skin.

In one example embodiment micro-particle 370 or 400 includes liposomes, microspheres, nano-spheres or nano-particles. In another example embodiment micro-particle 370 or 400 consists of first protective layer 420 as the next largest hollow sphere, and second protective layer 430 as outermost hollow sphere. This design may consist of one, two, or as many protective layers as required for a given micro-particle structural composition.

The layers of the micro-particle's structure includes but is not limited to lipid conglomerates or polymers preferably biodegradable.

In another example embodiment micro-particle 370 or 400 is prepared from at least one biocompatible lipid. In another example embodiment micro-particle 370 or 400 is prepared from at least one biocompatible polymer selected from the group consisting of polysaccharides, semi-synthetic polymers and synthetic polymers. In another example embodiment micro-particle 370 or 400 is prepared from the following:

(1) from a composition comprising dipalmitoylphosphatidylcholine, glycerol and propylene glycol.
(2) from a composition comprising dipalmitoylphosphatidylethanolamine and phosphatidic acid in an amount of from 0.5 to 30 mole percent.
(3) from a composition comprising dipalmitoylphosphatidylcholine and distearoylphosphatidyl-choline in an amount of from 70 to 100 mole percent.
(4) from a composition comprising: (I) a neutral lipid, (ii) a negatively charged lipid, and (iii) a lipid bearing a hydrophilic polymer; wherein the amount of said negatively charged lipid is greater than 1 mole percent of total lipid present, and the amount of lipid bearing a hydrophilic polymer is greater than 1 mole percent of total lipid present.

In another example embodiment micro-particle 370 or 400 comprises the following:
(1) a mono-layer.
(2) a polymer.
(3) a polysaccharide.
(4) a micelle system.
(5) a surfactant.

In operation, the micro-particles 400 are forced into the ultrasonically disrupted skin as shown in FIG. 3. After the particle is embedded in the dermis, the protective layer or layers surrounding the drugs, or therapeutic agents, or cosmetic are released into the skin in one or more of the following manners:
(1) the micro-particle dissolves or biodegrades in the skin with predetermined rate and the drugs, or therapeutic agents, or cosmetic are released. The rate of dissolution will depend on the design of the protective sheath and the number of sheaths surrounding the center core of the micro-particle.
(2) The micro-particles containing gas in their interior are burst open by application of an additional external ultrasound of an resonance frequency that matches the size of the micro-particles containing gas along with a drug, or therapeutic agent, or cosmetic. For example, when diameter of the gas containing micro-particle is 3 micrometers, which is convenient size for drug, or therapeutic, or cosmetic carrier, the resonance frequency is 2.2 MHz. By the large-amplitude vibration and the rise of the temperature caused by the resonance, the drug, or therapeutic agent, or cosmetic is released in to the skin.

Figure 5:
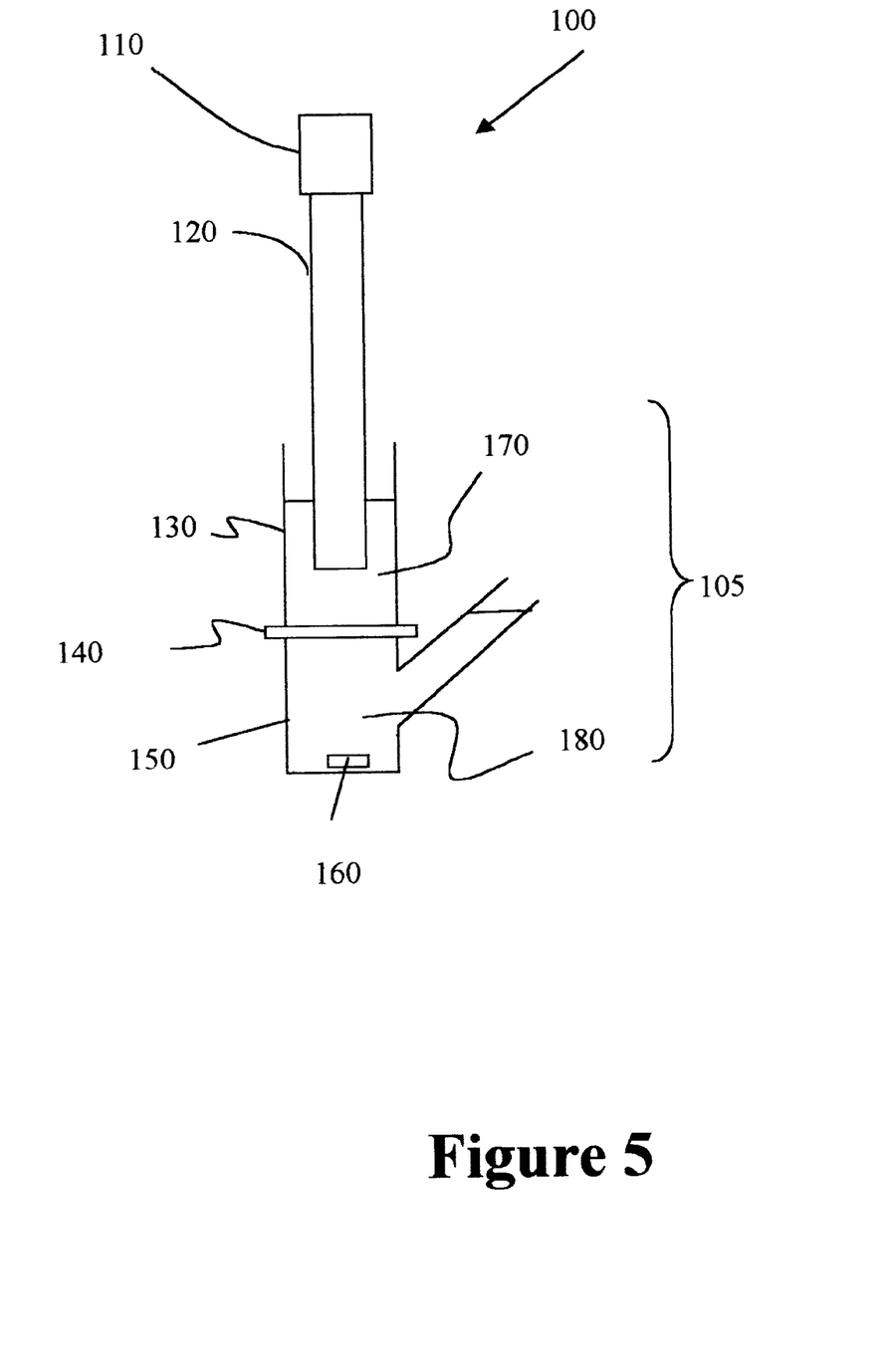

FIG. 5 shows Franz Cell apparatus 100 for determining infusion of micro-particles into the human cadaver epidermis 140 during exposure of the skin to ultrasound of 20 kHz and intensity of 19 W cm$^{-2}$. The apparatus 100 includes the ultrasound transducer 110 with horn 120 and Franz Cell assembly 105. The ultrasound horn 120 is electrically and mechanically connected to an ultrasound transducer 110. Ultrasound transducer 110 is electrically connected to a power supply (not shown). The ultrasound horn 120 is submerged in the micro-particles suspension 170 placed in the donor compartment 130. The exposure of the skin to the ultrasound causes formation of pores in the stratum corneum and transient micro-pores in the epidermis of the skin 140, which allow for transdermal flux of the micro-particles from the donor compartment 130 to the saline solution 180 in the receiver compartment 150.

Figure 6:
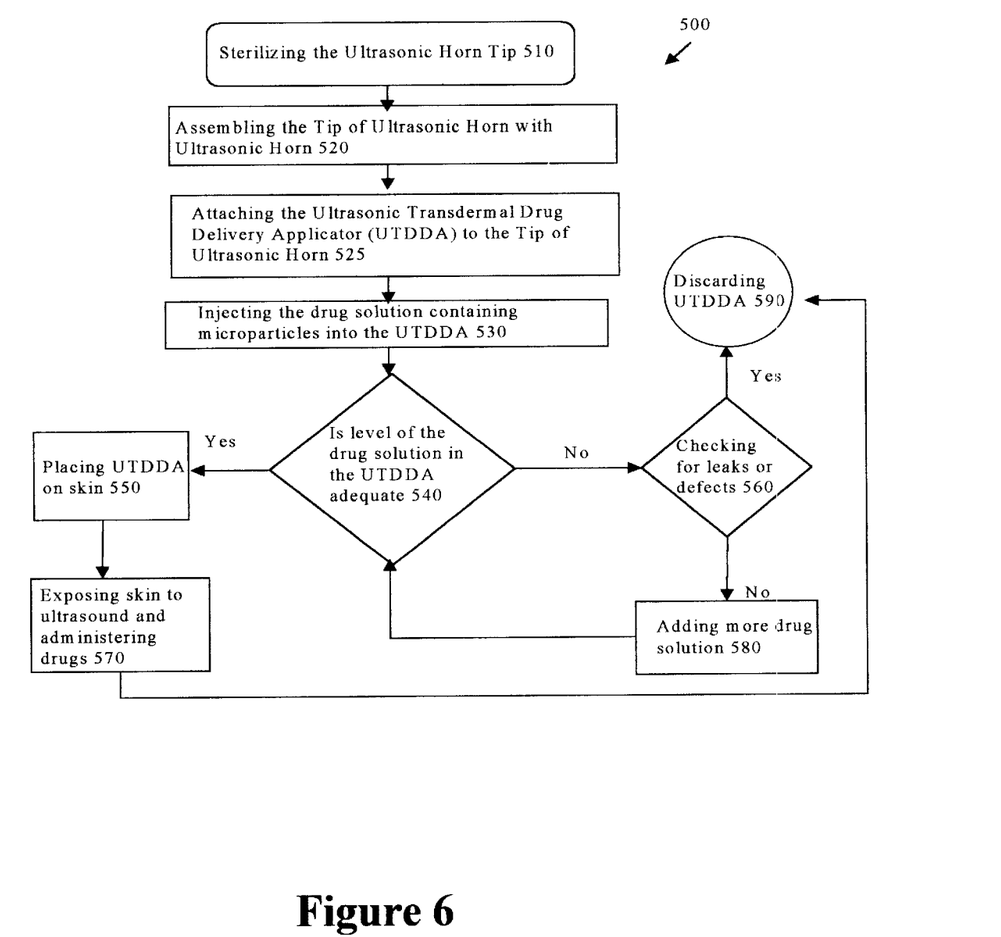

FIG. 6 is a method 500 for transdermal incorporation of micro-particles containing encapsulated drugs using sonoporation that includes the following steps:

Step 510: Sterilizing the Ultrasonic Horn Tip
The ultrasonic horn tip 270 may be sterilized using an ethylene oxide gas or by exposing the horn tip 270 to elevated heat/steam. The horn tip may also be pre-sterilized and sealed in a protective package. The method then proceeds to Step 520.

Step 520: Assembling the tip of Ultrasonic Horn with Ultrasound Horn
The sterilized ultrasonic horn tip 270 is attached to the ultrasound horn 80 by screwing the threaded tip into the ultrasound horn. The method then proceeds to Step 525.

Step 525: Attaching the Ultrasonic Transdermal Drug Delivery Applicator (UTDDA) to the Tip of Ultrasonic Horn
The tip of the ultrasonic horn 270 is inserted into the UTDDA 100 so that the O-rings 220 and 230 hold the assemblies together securely. The method then proceeds to Step 530.

Step 530: Injecting the microparticles suspension containing micro-particles into the UTDDA
The microparticles suspension 290 is introduced into the UTDDA 100 via the septum 240 using a hypodermic needle to inject the solution. The method then proceeds to Step 540.

Decision Step 540: Is level of the microparticles suspension in the UTDDA adequate
By visual inspection, the injected liquid level is compared to the level marking 260. If the microparticles suspension level is aligned with the marked level 260, the method proceeds to Step 550. If the levels are not aligned, the method proceeds to Step 560 to check for the source of inadequate solution level.

Step 550: Placing UTDDA on skin
The removable protective film 265 is removed from the UTDDA 100. Then the apparatus is oriented such that the porous membrane is fully flush with the skin surface (it must be basically perpendicular to the plane of the skin surface and arranged so that the tip of the horn 270 is immersed in the microparticles suspension 290). The method then proceeds to Step 570.

Decision Step 560: Checking for leaks or defects

If the microparticles suspension level is inadequate, the apparatus may be leaking or is defective. The apparatus is visually inspected to look for leaks or visible defects. If there are no other sources of error, the amount of solution may be inadequate to fill the reservoir, and the method proceeds to Step 580 to correct this problem. If the UTDDA 100 is leaking or is otherwise defective, the method proceeds to Step 590.

Step 570: Exposing skin to ultrasound and administering drugs

The power supply 30 is turned on and a timer, which is contained in power supply 30, is set to a predetermined length of ultrasound exposure (5–60 seconds). The ultrasound is turned on for a predetermined period of time that causes formation of the micropores 310 in the skin and subsequent transfer of the drug from the reservoir of the UTDDA 100 into the micropores formed. The method then proceeds to Step 590.

Step 580: Adding more microparticles suspension

If an inadequate volume of solution was initially added to the reservoir, more microparticles suspension 290 is added via the septum. The method then proceeds to Step 540.

Step 590: Discarding UTDDA

If the UTDDA 100 is defective, the applicator must be discarded and a new one used to administer the microparticles suspension 290. After the UTDDA 100 has been used once, it must be discarded. Prior to discarding the UTDDA 100, the power supply is set to a stand-by condition. The method ends after the UTDDA 100 has been discarded.

If the micro-particles embedded in the skin are to be burst open in order to release the content into the skin, the external ultrasound of the resonance frequency is applied to skin.

EXAMPLE

In the Franz Cell apparatus shown in FIG. 5, a 2% micro-particles suspension in saline was placed in the donor compartment over the heat-split human cadaver epidermis. The receiver compartment was filled with the saline solution. Ultrasound horn was submerged in micro-particles suspension at 6 mm height above the skin surface. Ultrasound of 20 kHz and intensity of 19W cm$^{-2}$ was turned on for periods of 15 sec and off for 59.9 sec. The total exposure time to ultrasound was 90 sec. The AC current of 1 V and 10 Hz was measured during the ultrasound exposure time (not shown) to determine skin permeability in presence of different size micro-particles. The following micro-particle sizes were investigated: 1.5 mm, 5.2 mm, 11.9 mm, 25 mm, 40 mm and 173 mm. The 2% suspensions in saline solution with micro-particles of the following sizes 1.5 mm, 5.2 mm, 11.9 mm, and 173 mm. were obtained from Seradyn Mitsubishi Kasei Corp., 1200 Madison Ave., Indianapolis, Ind. 46225. Particles of other two sizes 25 mm and 40 mm were obtained from Aldrich). The effect of the micro-particle size on the transdermal flux and skin conductivity is shown in Table 1.

The many features and advantages of the present invention are apparent from the detailed specification, and thus, it is intended by the appended claims to cover all such features and advantages of the described method and apparatus that follow the true spirit and scope of the invention. Furthermore, since numerous modifications and changes will readily occur to those of skill in the art, it is not desired to limit the invention to the exact construction and operation described herein. Moreover, the method and apparatus of the present invention, like related apparatus and methods used in medical applications tend to be complex in nature and are often best practiced by empirically determining the appropriate values of the operating parameters or by conducting computer simulations to arrive at a best design for a given application. Accordingly, other embodiments are within the scope of the following claims.

What is claimed is:

1. A method for sonoporation for intradermal delivery of a microparticles suspension containing microencapsulated drugs comprising: (1) providing a container having a first end and a second end, said second end being covered with a porous membrane covered by a removable protective film and containing said microparticles suspension; (2) submerging a removably connected tip of an ultrasound horn in said microparticles suspension containing microencapsulated drugs through said first end of the container; (3) placing said porous membrane in contact with said skin area; and (4) applying ultrasound radiation to said microparticles suspension containing microencapsulated drugs wherein said ultrasound radiation is applied at a frequency, an intensity, for a period of time, and at a distance from the skin, effective to generate cavitation bubbles, wherein said cavitation bubbles collapse and transfer their energy into the skin area thus causing the formation of pores in the skin area; and wherein said ultrasound radiation intensity and distance from the skin area are also effective in generating ultrasonic jets, said ultrasonic jets driving said microparticles suspension containing microencapsulated drugs through a porous membrane and said formed pores into the skin area, further comprising removing said protective film before placing said membrane in contact with the skin area.

2. The method of claim 1 wherein said membrane has pores with a diameter up to 100 micrometers.

3. The method of claim 1 wherein said membrane is hydrophobic.

4. The method of claim 1 wherein said tip comprises a flat distal end surface.

5. The method of claim 1 wherein said tip comprises a concave distal end surface.

6. The method of claim 1 wherein said tip comprises a flat distal end surface having a plurality of depressions.

7. The method of claim 1 wherein said tip comprises a body having markings indicating the amount of the microparticles suspension containing microencapsulated drugs contained in the container.

TABLE 1

Effect of particle size on transdermal flux and skin conductivity in presence of 20 kHz ultrasound at intensity of 19 W/cm$^2$.

| ULTRASOUND EXPOSURE TIME (sec) | AC CURRENT (1 v, 10 Hz) ACROSS THE SKIN ($\mu$A) | | | | | | |
|---|---|---|---|---|---|---|---|
| | WITHOUT MICRO-PARTICLES | PSFI 1.5 $\mu$m | POLYSTYRENE 5.2 $\mu$m | SDVB 11.9 $\mu$m | POLYETHYLENE 25 $\mu$m | POLYETHYLENE METHACRYLATE 40 $\mu$m | SDVB 173 $\mu$m |
| 0 | 36 | 23 | 37 | 34 | na | 24 | 40 |
| 15 | 53 | 40 | 45 | 50 | na | 28 | 52 |
| 30 | 55 | 50 | 50 | 60 | na | 35 | 60 |
| 45 | 67 | 90 | 70 | 83 | na | 36 | 61 |
| 60 | 76 | 128 | 85 | 120 | na | 46 | 61 |
| 75 | 124 | 140 | 110 | 225 | na | 50 | 62 |
| 90 | 151 | 165 | 180 | 290 | na | 51 | 65 |
| TOTAL PENETRATION OF SKIN BY MICROPARTICLES | NA | YES | YES | YES | YES | NO | NO |

8. The method of claim 1 wherein said container comprises: (1) an outer wall; (2) an inner wall; and (3) an absorbent wick placed between said inner and outer wall, said wick absorbing any excess microparticles suspension containing microencapsulated drugs that is not driven into the skin area through the formed pores.

9. The method of claim 8 wherein said wick comprises absorbent cellulose material, polyvinyl alcohol sponge or Sodium carboxymethylcellulose.

10. The method of claim 8 wherein said inner wall comprises first and second grooves, said tip comprises a body having first and second grooves and wherein said first and second grooves of the tip body are arranged opposite said first and second grooves of the container inner wall, the arrangement defining first and second spaces for accommodating a first and second o-rings, respectively.

11. The method of claim 8 wherein said container further comprises an inlet septum for filling said container with the solution.

12. The method of claim 1 wherein said container is a cylinder.

13. The method of claim 1 wherein said container comprises a transparent material.

14. The method of claim 1 wherein said container comprises a plastic material.

15. The method of claim 1 wherein the ultrasound frequency is 1 KHz to 1 MHz.

16. The method of claim 1 wherein the ultrasound frequency is 20 KHz.

17. The method of claim 1 wherein said ultrasound intensity is in the range of 5 W/cm.sup.2 and 55 W/cm.sup.2.

18. The method of claim 1 wherein the tip has a distal end located at a distance from said membrane in the range of 1 millimeter to 10 millimeters.

19. The method of claim 1 wherein said ultrasound radiation is continuous.

20. The method of claim 1 wherein said ultrasound radiation is pulsed.

21. The method of claim 1 wherein said period of time is in the range of about 30 seconds to 5 minutes of continuous exposure to ultrasound radiation.

22. The method of claim 1 wherein said period of time is in the range of about 10 minutes to 20 minutes of pulsed exposure to ultrasound radiation with a 5% duty cycle.

23. The method of claim 1 wherein said formed pores have a diameter in the range of 1 micrometer to 100 micrometers.

24. A method for sonoporation for intradermal delivery of a microparticles suspension containing microencapsulated drugs comprising: (1) providing a container containing a predetermined amount of said microparticles suspension containing microencapsulated drugs and having a first end and a second end, said second end being covered with a porous membrane; (2) submerging a tip of an ultrasound horn in said microparticles suspension containing microencapsulated drugs through said first end of the container; (3) placing said porous membrane in contact with said skin area; and (4) applying ultrasound radiation to said microparticles suspension containing microencapsulated drugs wherein said ultrasound radiation is applied at a frequency, an intensity, for a period of time, and at a distance from the skin, effective to generate cavitation bubbles, wherein said cavitation bubbles collapse and transfer their energy into the skin area thus causing the formation of pores in the skin area; and wherein said ultrasound radiation intensity and distance from the skin area are also effective in generating ultrasonic jets, said ultrasonic jets driving said microparticles suspension containing microencapsulated drugs through a porous membrane and said formed pores into the skin area, wherein said tip is removably connected to said ultrasound horn.

25. The method of claim 24 wherein said membrane has pores with a diameter of up to 100 micrometers.

26. The method of claim 24 wherein said membrane is hydrophobic.

27. The method of claim 24, further comprising sterilizing said tip before attaching it to said ultrasound horn.

28. The method of claim 24 wherein said tip comprises a flat distal end surface.

29. The method of claim 24 wherein said tip comprises a concave distal end surface.

30. A method for sonoporation for intradermal delivery of a microparticles suspension containing microencapsulated drugs comprising: (1) providing a container containing a predetermined amount of said microparticles suspension containing microencapsulated drugs and having a first end and a second end, said second end being covered with a porous membrane; (2) submerging a tip of an ultrasound horn in said microparticles suspension containing microencapsulated drugs through said first end of the container; (3) placing said porous membrane in contact with said skin area; and (4) applying ultrasound radiation to said microparticles suspension containing microencapsulated drugs wherein said ultrasound radiation is applied at a frequency, an intensity, for a period of time, and at a distance from the skin, effective to generate cavitation bubbles, wherein said cavitation bubbles collapse and transfer their energy into the skin area thus causing the formation of pores in the skin area; and wherein said ultrasound radiation intensity and distance from the skin area are also effective in generating ultrasonic jets, said ultrasonic jets driving said microparticles suspension containing microencapsulated drugs through a porous membrane and said formed pores into the skin area, wherein said tip comprises a flat distal end surface having a plurality of depressions.

31. A method for sonoporation for intradermal delivery of a microparticles suspension containing microencapsulated drugs comprising: (1) providing a container containing a predetermined amount of said microparticles suspension containing microencapsulated drugs and having a first end and a second end, said second end being covered with a porous membrane; (2) submerging a tip of an ultrasound horn in said microparticles suspension containing microencapsulated drugs through said first end of the container; (3) placing said porous membrane in contact with said skin area; and (4) applying ultrasound radiation to said microparticles suspension containing microencapsulated drugs wherein said ultrasound radiation is applied at a frequency, an intensity, for a period of time, and at a distance from the skin, effective to generate cavitation bubbles, wherein said cavitation bubbles collapse and transfer their energy into the skin area thus causing the formation of pores in the skin area; and wherein said ultrasound radiation intensity and distance from the skin area are also effective in generating ultrasonic jets, said ultrasonic jets driving said microparticles suspension containing microencapsulated drugs through a porous membrane and said formed pores into the skin area, wherein said tip comprises a body having markings indicating the amount of the microparticles suspension containing microencapsulated drugs contained in the container.

32. The method of claim 31 further comprising checking the amount of said microparticles suspension containing microencapsulated drugs contained in said container before applying said ultrasound radiation.

33. The method of claim 32 further comprising adding microparticles suspension containing microencapsulated drugs to said container.

34. A method for sonoporation for intradermal delivery of a microparticles suspension containing microencapsulated drugs comprising: (1) providing a container containing a predetermined amount of said microparticles suspension containing microencapsulated drugs and having a first end and a second end, said second end being covered with a porous membrane; (2) submerging a tip of an ultrasound horn in said microparticles suspension containing microencapsulated drugs through said first end of the container; (3) placing said porous membrane in contact with said skin area; and (4) applying ultrasound radiation to said microparticles suspension containing microencapsulated drugs wherein said ultrasound radiation is applied at a frequency, an intensity, for a period of time, and at a distance from the skin, effective to generate cavitation bubbles, wherein said cavitation bubbles collapse and transfer their energy into the skin area thus causing the formation of pores in the skin area; and wherein said ultrasound radiation intensity and distance from the skin area are also effective in generating ultrasonic jets, said ultrasonic jets driving said microparticles suspension containing microencapsulated drugs through a porous membrane and said formed pores into the skin area, wherein said container comprises: (1) an outer wall; (2) an inner wall; and (3) an absorbent wick placed between said inner and outer wall, said wick absorbing any excess microparticles suspension containing microencapsulated drugs that is not driven into the skin area through the formed pores.

35. The method of claim 24 wherein said ultrasound frequency is 20 KHz.

36. The method of claim 24 wherein said ultrasound intensity is in the range of 5 W/cm.sup.2 and 55 W/cm.sup.2.

37. The method of claim 24 wherein said tip has a distal end located at a distance from said membrane in the range of 1 millimeter to 10 millimeters.

38. The method of claim 24 wherein said ultrasound radiation is continuous.

39. The method of claim 24 wherein said ultrasound radiation is pulsed.

40. The method of claim 24 wherein said period of time is in the range of about 30 seconds to 5 minutes of continuous exposure to ultrasound radiation.

41. The method of claim 24 wherein said period of time is in the range of about 10 minutes to 20 minutes of pulsed exposure to ultrasound radiation with a 5% duty cycle.

42. The method of claim 24 wherein said formed pores have a diameter in the range of 1 micrometer to 200 micrometers.

43. The method of claim 24 wherein the ultrasound frequency is 1 KHz to 5 MHz.

* * * * *

UNITED STATES PATENT AND TRADEMARK OFFICE
CERTIFICATE OF CORRECTION

PATENT NO. : 6,712,805 B2
DATED : March 30, 2004
INVENTOR(S) : Ludwig J. Weimann It is certified that error appears in the above-identified patent and that said Letters Patent is hereby corrected as shown below:

<u>Title page,</u>
Item [73], Assignee, please add the following :
-- Ultra-Sonic Technologies, LLC
St. Albans, Vermont 05478 --

Signed and Sealed this

Twenty-seventh Day of July, 2004

JON W. DUDAS
*Acting Director of the United States Patent and Trademark Office*